United States Patent [19]

Chen

[11] 4,121,583
[45] Oct. 24, 1978

[54] METHOD AND APPARATUS FOR ALLEVIATING ASTHMA ATTACKS

[76] Inventor: Wen Yuan Chen, 770 Jersey St., Denver, Colo. 80220

[21] Appl. No.: 704,762

[22] Filed: Jul. 13, 1976

[51] Int. Cl.² .......................................... A61M 15/00
[52] U.S. Cl. .................................................. 128/192
[58] Field of Search ............... 128/212, 186, 187, 188, 128/192, 193, 142 R, 194

[56] References Cited

U.S. PATENT DOCUMENTS

| 437,070 | 9/1890 | Wiesebrock | 128/192 |
|---|---|---|---|
| 2,091,034 | 8/1937 | Duncan | 128/192 |
| 3,366,775 | 1/1968 | Mycue | 128/192 |
| 3,526,226 | 9/1970 | Stern | 128/192 |
| 3,638,926 | 2/1972 | Melville et al. | 128/192 |
| 3,695,267 | 10/1972 | Hirtz et al. | 128/192 |
| 3,903,883 | 9/1975 | Pecina et al. | 128/193 |
| 3,916,891 | 11/1975 | Freytag et al. | 128/192 |
| 4,010,748 | 3/1977 | Dobritz | 128/192 |

FOREIGN PATENT DOCUMENTS

313,542  3/1972  U.S.S.R. .................................. 128/212

Primary Examiner—Henry J. Recla
Attorney, Agent, or Firm—John E. Reilly

[57] ABSTRACT

A method and apparatus for alleviating asthmatic attacks minimizes heat and water loss in the respiratory tract of the asthma sufferer. A portable embodiment of the apparatus includes an elongated tube having a fibrous material dispersed around the inner surface for holding water, a heating filament cylindrically coiled against the fibrous material and interconnected with a battery attached to the sufferer, and fiber wrapped around the filament for conveying the water located in the fibrous material to the surface of the filament for evaporation. The method for alleviating asthmatic attacks includes the steps of heating and evaporating water, heating the atmospheric air, and inspiring the heated atmospheric air and vaporized water.

13 Claims, 9 Drawing Figures

Fig_1

Fig_2

Fig_3

Fig_4

Fig_5

Fig_6

Fig_7

Fig_10

Fig_8

Fig_9

METHOD AND APPARATUS FOR ALLEVIATING ASTHMA ATTACKS

BACKGROUND OF THE INVENTION

1. Field of the Invention

The present invention relates generally to an aid for alleviating asthmatic attacks.

2. Description of the Prior Art

People having asthma who exercise generally incur the clinical signs and symptoms of an acute asthmatic attack. In the laboratory exercise testing is frequently used to study this exercise-induced asthma.

The nature of exercise-induced asthma is not clear. Various researchers have suggested numerous mechanisms for causing asthmatic attacks following exercise. One suggested mechanism is the stimulation of the airway receptors that trigger a vagal reflex.

Stanescu, D. C., and D. B. Techulescu. 1970. Exercise- and cough-induced asthma. *Respiration.* 27:377–383.

Simonsson, B. G., B. E. Skoogh, and B. Ekstrom-Jodal. 1972. Exercise-induced airways constriction. *Thorax.* 27:169–180.

Kiviloog, J. 1973. Bronchial reactivity to exercise and metacholine in bronchial asthma. *Scan. J. Respir. Dis.* 54:347–358.

Crompton, G. K. 1968. An unusual example of exercise-induced asthma. *Thorax.* 23:165–167.

Other researchers suggest hypocapnia.

Rebuck, A. S., and J. Read. 1968. Exercise-induced asthma. *Lancet.* 2:429–431.

Fisher, H. K., P. Holton, R. ST. J. Buxton, and J. A. Nadel. 1970. Resistance to breathing during exercise-induced asthma attacks. *Am. Rev. Respir. Dis.* 101:885–896.

Some researchers suggest metabolic acidosis,

Seaton, A., G. Davies, D. Gaziano, and R. O. Hughes. 1969. Exercise-induced asthma. *Br. Med. J.* 3:556–558.

While other researchers suggest ventilation and profusion abnormalities.

Katz, R. M., B. J. Whipp, E. M. Heimlich, and K. Wasserman. 1971. Exercise-induced bronchospasm, ventilation and blood gases in asthmatic children. *J. Allergy.* 47:148–158.

And finally, some investigators suggest the release of pharmacologically activate mediators.

Simonsson, B. G., B. E. Skoogh, and B. Ekstrom-Jodal. 1972. Exercise-induced airways constriction. *Thorax.* 27:169–180.

McNeill, R. S., J. R. Nairn, J. S. Millan, and C. G. Ingram. 1966. Exercise-induced asthma. *Q. J. Med.* 35:55–67.

The method and apparatus of the present invention for alleviating exercise-induced asthma attacks has not been investigated nor even suggested in the above prior art known by the inventor. The method and apparatus of the present invention concerns the airway heat and water loss during exercise. For example, room air at 23° C. and 30% relative humidity (RH) contains 6.1 mg. of water per liter of air. The expired air measured at the lip is 33° C. and contains 36 mg. of water per liter.

Webb, P. 1951. Air temperatures in respiratory tracts of resting subjects in cold. *J. Appl. Physiol.* 4:378–382.

Ingelstedt, S. 1956. Studies on the conditioning of air in the respiratory tract. *Acta Otolaryngol.* Suppl. 131:7–80.

Green, I. D., and M. S. Nesarajah. 1968. Water vapour pressure of end-tidal air of normals and chronic bronchitis. *J. Appl. Physiol.* 24:229–231.

Thus, in breathing one liter of room air, a person loses approximately 30 mg. of water and 18 calories of heat. At rest with normal ventilation of 10 liters of air per minute, the water and heat losses from the respiratory tract would be equivalent to 300 mg. and 180 calories per minute respectively. During moderate exercise, these values may increase five times or more. The method and apparatus of the present invention is designed to minimize heat and water loss in the asthma sufferer's lungs.

Clear and convincing evidence of the operability and utility of the method and apparatus of the present invention appears in "Heat and Water Loss from the Airways and Exercise-Induced Asthma" by W. Y. Chen and D. J. Horton. The abstract of the above-identified paper is reproduced below:

Exercise-induced asthma was studied in eight asthmatics using various conditions of inspired air during exercise. The exercise consisted of walking on a treadmill for 10 minutes, with a speed and grade elevation adjusted to achieve the target heat rate of approximately 90% of predicted maximum. Pulmonary function tests were performed pre- and post-exercise to determine exercise-induced asthma. With inspired air at 23° C. and 15% relative humidity (RH), the post-exercise forced expiratory volume in one second ($FEV_1$), maximal mid-expiratory flow rate (MMEF), and specific airway conductance (SGaw) decreased to an average of 69%, 59%, and 38% of the pre-exercise baseline respectively. In contrast, the exercise-induced asthma was clearly prevented in all subjects by using inspired air at 37° C. and 100% RH, when the post-exercise $FEV_1$, MMEF, and SGaw were 99%, 100%, and 91% of the baseline respectively. Inspiration of warm, dry air or humid room air partially prevented exercise-induced asthma. The results indicate that the primary stimulus for exercise-induced asthma is the heat loss and/or water loss from the airways during exercise. (*Physiologist*, August, 1976)

Due to the unexpected and surprising results discovered by the inventor and reported in the abovecited reference, parts of the paper are reproduced in the specification below to demonstrate the primary novelty and usefulness this invention provides for asthma sufferers over all other prior art approaches. Based upon the method and apparatus of the present invention, substantial numbers of asthma sufferers will be able to exercise either indoors or outdoors.

The results indicate that sufferers can have asthma attacks alleviated by inspiring air between 30° C. to 40° C., and 30% RH to 100% RH, more specifically, exercise-induced asthma attacks are inhibited by inspiring air between 37° C. and 40° C. and 80% RH to 100% RH. Exercise-induced asthma attacks were clearly prevented by inspiring air between 37° C. to 40° C. and 100% RH.

OBJECTS OF THE INVENTION

It is an object of the present invention to provide a new and improved apparatus for alleviating asthma attacks by substantially reducing heat loss in the respiratory system of an asthma sufferer.

It is another object of the present invention to provide a new and improved apparatus for alleviating asthma attacks by substantially reducing water loss in the airways of an asthma sufferer.

It is another object of the present invention to provide a new and novel apparatus for inhibiting the occurrence of asthma attacks by substantially reducing both the heat and water loss in the respiratory tract of the sufferer.

It is another object of the present invention to provide a new and novel portable apparatus for use by an asthma sufferer in alleviating exercise-induced asthma attacks wherein means is provided to store air during the time interval between the inhalation and exhalation of air by the sufferer, means for increasing the heat content of the stored air, means for vaporizing water into the air, and means for delivering the high heat content air and vaporized water into the lungs of the sufferer upon inhalation.

It is another object of the present invention to provide a new and improved apparatus for use by an asthma sufferer in alleviating asthma attacks which includes means for humidifying the air, means receptive of the humidified air for storing the air, means for holding water, means cooperative with the holding means for heating the water, means operative upon the stored humidified air for mixing the humidified air with evaporated water above the surface of the heated water, and means for delivering the mixed air into the lungs of the sufferer.

It is another object of the present invention to provide a new and improved method for alleviating asthma attacks of an asthma sufferer comprising the step of reducing heat loss in the respiratory system of the sufferer.

It is another object of the present invention to provide a new and improved method for alleviating asthma attacks of an asthma sufferer having the steps of increasing heat content of the atmospheric air and inhaling the higher heat content atmospheric air.

It is another object of the present invention to provide a new and novel method for alleviating asthma attacks of an asthma sufferer having the step of reducing water loss in the respiratory tract of the sufferer.

It is another object of the present invention to provide a new and novel method for alleviating asthma attacks of an asthma sufferer having the steps of reducing heat and water loss in the respiratory system of the sufferer.

It is another object of the present invention to provide a new and novel method for alleviating asthma attacks of an asthma sufferer having the steps of humidifying air, storing the humidified air, heating water, and passing the humidified air over the heated water and into the lungs of the sufferer.

SUMMARY OF THE INVENTION

A portable embodiment of the apparatus of the present invention includes a breathing valve interconnected at one end to an elongated tube. As the asthma sufferer inhales, atmospheric air is drawn into the elongated tube and is heated and humidified. The inhalation of heated and humidified air substantially reduces heat and water loss in the respiratory system of the sufferer. A fibrous material is disposed around the interior surface of the tube and is saturated with water. A heating filament is cylindrically coiled against the fibrous material on the interior surface of the tube and is interconnected with a battery. A thermistor circuit is provided to control the temperature of the humidified air in the chamber defined by the interior of the tube. Fiber is disposed around the heating filament for directing the stored water from the fibrous material to the surface of the filament for evaporation. The elongated tube may be discarded and replaced after each use by the sufferer.

Another embodiment of the apparatus of the present invention adaptable for the hospital bed includes a humidifier for adding moisture to atmospheric air, a reservoir receptive of the humidified air for storing the air, a container holding water and a heater disposed below the water for heating the water to a desired temperature thereby evaporating some of the water into the region above the surface of the water, and means for passing the humidified air from the storage reservoir into the heated air containing evaporated water above the surface of the water and into the face tent of the sufferer for inspiration. A vacuum pump is used to deliver the air mixture to the asthma sufferer at a controlled rate. The humidifier and the heater may be varied to adjust the heat and to adjust the water content to meet the needs of the patient. The delivered air into the lungs of the patient substantially contains vaporized water rather than particulate water.

The method of the present invention includes the steps of heating water and the atmospheric air, adding vaporized water to the air, and inhaling the warm, humidified air thereby minimizing heat and water loss in the respiratory tract of the sufferer.

Other objects, advantages and capabilities of the present invention will become more apparent as the description proceeds, taken in conjunction with the accompanying drawings.

DESCRIPTION OF THE PREFERRED EMBODIMENT

1. Experimental Results.

The following is substantially reproduced from the paper by the inventor cited above. Appropriate sections however, have been modified to provide positive references to the drawings.

The subjects of the experiment were eight uncomplicated asthmatics, four hospitalized patients and four hospital employees. All subjects had been familiarized with treadmill walking prior to the study, and acknowledged having symptoms of asthma induced by exercise. The physical characteristics of the subjects and their medications are presented below in Table 1.

TABLE 1

| Subject | Sex | Age yr | Height cm | Weight kg | Medication | Amount mg | Frequency |
| --- | --- | --- | --- | --- | --- | --- | --- |
| DH | M | 30 | 177 | 70 | Aminophylline | 200 | 4 tms. daily |
|    |   |    |     |    | Metaproterenol | 20 | 4 tms. daily |
| AG | M | 15 | 162 | 52 | Aminophylline | 400 | 4 tms. daily |
|    |   |    |     |    | Terbutaline | 5 | 4 tms. daily |
| PB | F | 25 | 147 | 67 | Beclomethasone | 0.1 | 4 tms. daily |
|    |   |    |     |    | Prednisone | 12½ | every other day |
|    |   |    |     |    | Aminophylline | 400 | 4 tms. daily |
| DR | F | 14 | 170 | 56 | Theophylline | 375 | 3 tms. daily |
| PG | M | 23 | 170 | 69 | Methylprednisolone | 18 | every other day |
|    |   |    |     |    | Aminophylline | 400 | 4 tms. daily |
|    |   |    |     |    | Ephedrine | 30 | 4 tms. daily |
| CW | F | 23 | 170 | 61 | None |   |   |
| JM | F | 22 | 160 | 53 | None |   |   |
| LK | F | 13 | 147 | 39 | Prednisone | 35 | every other day |
|    |   |    |     |    | Aminophylline | 450 | 3 tms. daily |
|    |   |    |     |    | Terbutaline | 5 | 3 tms. daily |

All experiments were performed in the same hour of the day for the same subject to avoid any possible diurnal fluctuations. In the subjects taking bronchodilators, the tests were conducted 1½ hours prior to their next scheduled dose of medication. In those taking alternate-day corticosteroids, testing was done on the off-steroid day. An individual subject was usually tested every other day, with the entire series of testing completed within two weeks.

The exercise consisted of walking on a treadmill 5 (Quinton Instruments) for 10 minutes, with a speed and elevation adjusted to achieve the target heart rate for at least the last 3 minutes of exercise.

Lange Andersen, K., R. J. Shephard, H. Denolin, E. Varnauskas, and R. Masironi. 1971. Fundamentals of Exercise Testing. World Health Organization. 45.

The target heart rates for the age groups of 10–19, 20–29, and 30–39 years were 180, 170 and 160 beats per minute respectively.

The experiments were performed in two series. In the first series all eight subjects were tested using two different inspired air conditions, designated as condition I and condition IV, during the treadmill exercise. Condition I was room air that was 23±1° C. (YSI Telethermometer, Model 44 TD) with a relative humidity (RH) of 15±5% (Bendix Psychron, Model 566). Condition IV was fully humidified warm air that was 37±0.5° C. and 100% RH. In the second series of experiments two additional inspired air conditions, conditions II and III, were performed in four of the subjects. Condition II was inspired air at 37±1° C. and 10±2% RH, and condition III was inspired air at 23±1° C. and 95±5% RH. After the termination of exercise, the subject continued to breathe in the given inspired air as long as hyperventilation was still obvious, which was a period lasting approximately 2 minutes. The conditions of inspired air were administered randomly. Experiments were repeated in some subjects after completion of the series to assure reproducibility of results and that there was no training effect.

Figure 1:
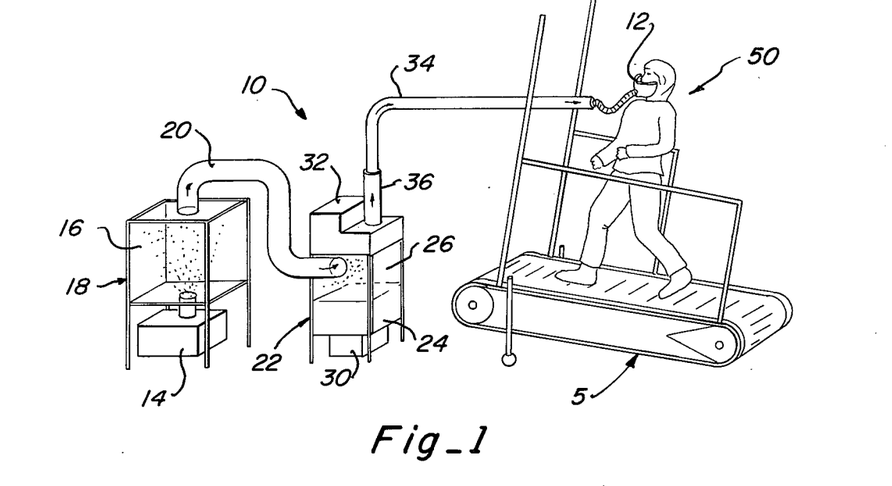
FIG. 1 is a schematic representation of one embodiment of the apparatus of the present invention illustrating the technique by which operability data was collected.

All four conditions of inspired air were delivered using the apparatus 10 of the present invention and a vinyl face tent 12 (Hudson Face Tent No. 1095). The experimental set-up is shown in FIG. 1.

To assess pulmonary functions, a body plethysmograph (Collins, Inc.) and a wedge spirometer (Med Science) were applied to determine the following indices: airway resistance (Raw), thoracic gas volume (Vtg), specific airway conductance (SGaw), forced vital capacity (FVC), forced expiratory volume in one second ($FEV_1$), $FEV_1$/FVC, maximal mid-expiratory fow rate (MMEF), and the flow-volume curve. The interconnections for these instruments are not shown. The body plethysmographic measurements always preceded the spirometric determinations. For each condition of inspired air, the pulmonary function tests were taken prior to exercise (the baseline measurement) and fixe to twelve minutes after the termination of exercise (the post-exercise measurement).

The experimental apparatus 10 comprises a humidifier 14 for injecting humidified air 16 into a reservoir or storing area 18. The stored humidified air 16 is delivered through an interconnecting conduit 20 into a second reservoir 22 containing water 24 and vaporized water 26. A heater 30 is disposed below the water 24 to heat the water 24 to a desired temperature. Heat is thereby conveyed into the evaporated water and air 26. An air pump 32 forces the air from the reservoir 22 into a thermally insulated delivery conduit 34 which accesses the tent mask 12. In the delivery conduit 34 is an air flow controller 36 for controlling the flow of the conditioned air to the tent mask 12 for breathing by the asthma sufferer 50.

The humidifier 14 is conventional and outputs into the reservoir 18 humidified air 16. This air contains droplets or particles of water suspended in air. The reservoir 16 is constructed from conventional material that does not rust or otherwise deteriorate upon contact with the humidified air 16. While in reservoir 18 most of the particles of water suspended in the air evaporate so that the water becomes gaseous. Conduit 20 delivers the humidified air into the second reservoir at a position just above the surface of the water 24. The water 24 is heated to a desired temperature by the heater 30 and produces gaseous water above the water due to the heated water. Furthermore, any remaining particulate water coming from conduit 20 becomes vaporized due to the heat. The mixture of heated air and vaporized water is delivered through the thermally insulated delivery conduit 34 into the face mask 12. The apparatus as shown provides means for adjusting the humidity, as vaporized water, being delivered into the sufferer 50 through appropriate controls found on the humidifier 14 and temperature of water 24. The apparatus 10 is designed to provide vaporized water at varying concentrations in air which also may be of varying temperatures. This is opposed to conventionally available nebulizers which suspend particles, albeit very fine particles, of water into the air. Such particles of water require large amount of heat to vaporize.

Table 2 below shows the changes in three representative indices of pulmonary function following exercise using inspired air condition I (23° C., 15% RH) and condition IV (37° C., 100% RH).

TABLE 2

| Subject | Inspired Air Conditions | | | | | |
|---|---|---|---|---|---|---|
| | I | | | IV | | |
| | $FEV_1$ | MMEF | SGaw | $FEV_1$ | MMEF | SGaw |
| DH | 33 | 40 | 14 | 93 | 105 | 100 |
| AG | 44 | 34 | * | 97 | 94 | * |
| PB | 59 | 52 | 17 | 108 | 104 | 81 |
| DR | 79 | 73 | 50 | 100 | 99 | 100 |
| PG | 88 | 60 | 33 | 105 | 94 | 88 |
| CW | 87 | 72 | 46 | 100 | 102 | 82 |
| JM | 85 | 68 | 65 | 100 | 97 | 93 |
| LK | 81 | 72 | * | 92 | 108 | * |
| Average | 69 | 59 | 38 | 99 | 100 | 91 |

*Subject unable to perform test.

Under condition I, the post-exercise $FEV_1$, MMEF, and SGaw decreased from the pre-exercise value to an average of 69%, 59%, and 38% of the baseline respectively. In contrast, the exercise-induced asthma was clearly prevented in all eight subjects under condition IV, when the post-exercise $FEV_1$, MMEF, and SGaw were 99%, 100%, and 91% of the pre-exercise baseline respectively.

Figure 2:
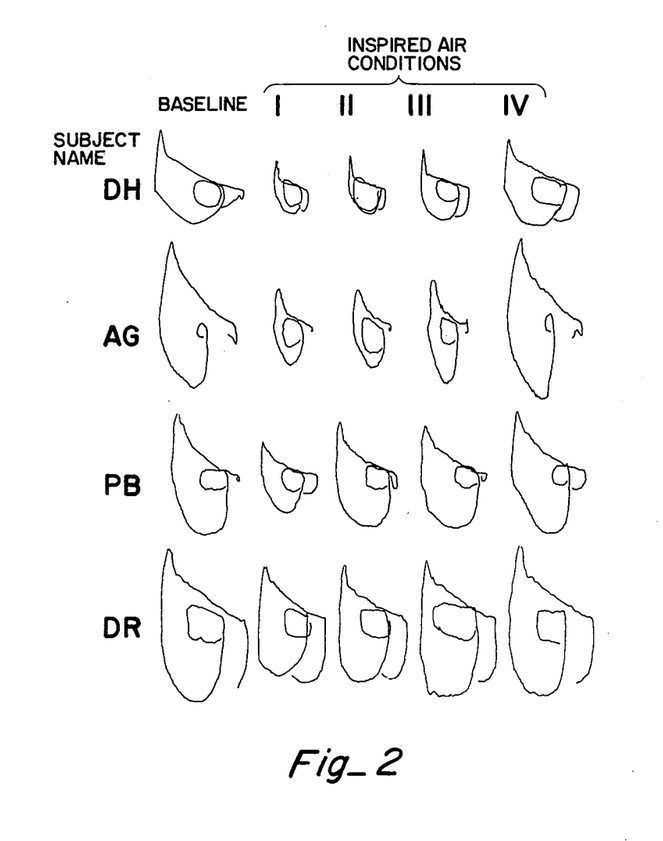
FIG. 2 is an illustration showing the various degrees of exercise-induced asthma shown in flow-volume curves.

In the second series of experiments two additional conditions, condition II and III, were performed in four of the subjects. For each subject FIG. 2 shows the flow-volume curve at baseline, which was very similar in all four testing conditions, and the post-exercise curves under the four inspired air conditions. The exercise-induced asthma was the most severe in condition I, progressively less in conditions II and III, and the least in condition IV, where the post-exercise flow volume curves were almost identical to the baseline curves.

Figure 3:
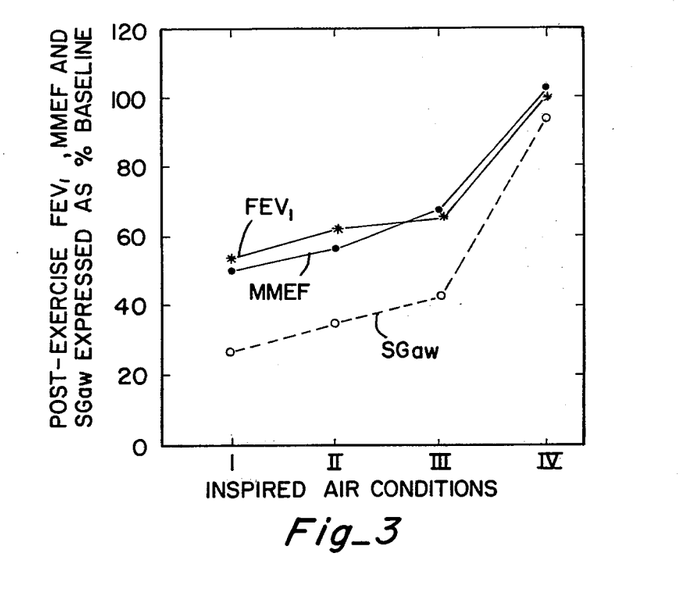
FIG. 3 is a graph showing the severity of exercise-induced asthma shown in three representative pulmonary function indices.

Table 3 below shows the post-exercise $FEV_1$, MMEF, and SGaw under the four conditions; a similar trend of improvement from condition I to IV is seen in all subjects. FIG. 3 shows the average post-exercise $FEV_1$, MMEF, and SGaw under the four conditions.

TABLE 3

| Index | Subject Name | Inspired Air Conditions | | | |
|---|---|---|---|---|---|
| | | I | II | III | IV |
| $FEV_1$ | DH | 33 | 40 | 51 | 93 |
| | AG | 44 | 51 | 53 | 97 |
| | PG | 59 | 75 | 76 | 108 |
| | DR | 79 | 82 | 82 | 100 |
| | Average | 54 | 62 | 66 | 100 |
| MMEF | DH | 40 | 46 | 61 | 105 |
| | AG | 34 | 41 | 64 | 94 |
| | PG | 52 | 58 | 66 | 104 |

TABLE 3-continued

| Index | Subject Name | Inspired Air Conditions | | | |
|---|---|---|---|---|---|
| | | I | II | III | IV |
| | DR | 73 | 78 | 77 | 99 |
| | Average | 50 | 56 | 67 | 101 |
| SGaw | DH | 14 | 25 | 25 | 100 |
| | AG* | — | — | — | — |
| | PG | 17 | 25 | 32 | 81 |
| | DR | 50 | 56 | 71 | 100 |
| | Average | 27 | 35 | 43 | 94 |

*Subject Unable to Perform Test.

The results demonstrate that the stimulus which triggers exercise-induced asthma can be removed by providing warm, humidified inspired air during exercise. Therefore, exercise-induced asthma must be related to the loss of heat and/or water from the respiratory tract during exercise.

In common environments, the inspired air gains heat and humidity as it moves toward the alveoli, and becomes fully saturated with water at body temperatures when reaching the alveoli.

Dery, R. 1971. Humidity in Anaesthesiology IV: Determination of the alveolar humidity and temperature in dog. *Can. Anaesth. Soc. J.* 18:145-151.

Cole, P. 1953. Further observations on the conditioning of respiratory air. *J. Laryngol. Oto.* 67:669-681.

To accomplish this, there is a continual transfer of heat and water from the respiratory tract to the inspired air. The alveolar air contains 43 mg of water per liter at body temperature, and only 20 to 30% of this water and heat is recovered when it leaves the body during normal nasal respirations.

Cole, P. 1953. Further observations on the conditioning of respiratory air. *J. Laryngol. Oto.* 67:669-681.

Toremalm, N. G. 1960. A heat-and-moisture exchanger for post-tracheotomy care. *Acta Otolaryngol.* 52:461-472.

Assuming in a given subject that the total ventilation during exercise was identical in the four experimental conditions, and that the proportion of heat and water recovered was the same in each exercise testing, the relative magnitude of the heat and water loss in each condition may be compared. This is accomplished by calculating the heat and water gradient between the alveolar air and the inspired air. The heat loss in one liter of expired air can be determined from the sum of the following three components:

$$Ha = Ma \times Sa \times (Tb - Ti), \tag{1}$$

$$Hw = Mw \times Sw \times (Tb - Ti), \text{ and} \tag{2}$$

$$H(r+q) = (0.043 - Mw) \times (576 + 37). \tag{3}$$

Where Ha is the heat loss due to the air temperature difference, in cal;
Ma is the mass of air in one liter, in g;
Sa is the specific heat of air;
Tb is the body temperature, in ° C.;
Ti is the inspired air temperature, in ° C.;
Hw is the heat loss due to the water temperature difference, in cal;
Mw is the mass of water in one liter of inspired air, in g;
Sw is the specific heat of water;
H(r+q) is the heat loss due to humidifying the inspired air, in cal;
r is the heat of vaporization;
q is the heat of water;

0.043 is the mass of water in g in saturated air at 37° C.;

576 is the heat of vaporization, in cal/g; and 37 is the heat of water at 37° C. body temperature, in cal/g.

Figure 4:
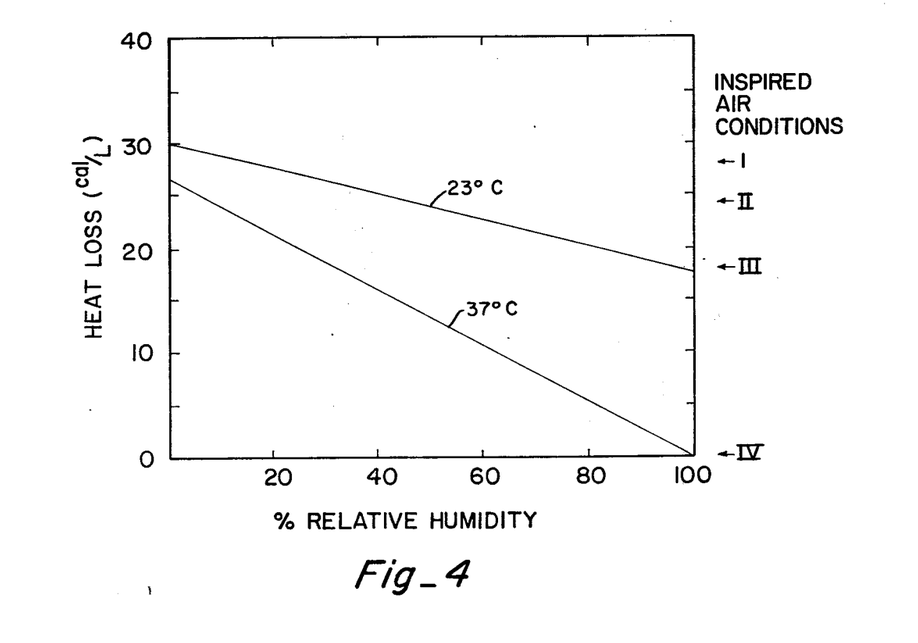
FIG. 4 is a graph showing the calculated respiratory heat loss with inspired air of 23° C. and 37° C. at various relative humidities.
Figure 5:
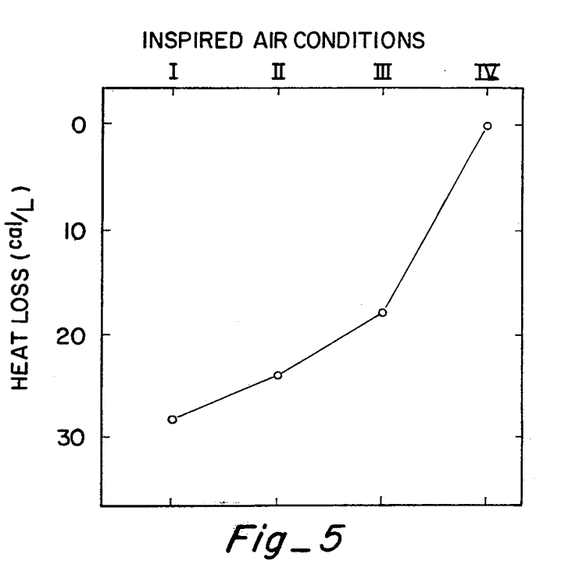
FIG. 5 is a graph showing the calculated respiratory heat loss for various inspired air mixtures.

With the above calculations, the heat loss under the inspired air of 23° C. and 37° C. at various relative humidities is obtained and shown in FIG. 4. The heat loss corresponding to the four inspired air conditions is presented in FIG. 5. Note that the degree of exercise-induced asthma under different inspired air conditions shown in FIG. 3 is similar to the extent of heat loss in the corresponding condition shown in FIG. 5.

The evaporative heat loss constitutes the major portion of the total heat loss from the respiratory tract. Therefore, the amount of water loss is approximately proportional to the extent of heat loss. Either heat or water loss may be the primary stimulus of exercise-induced asthma. The present experiments were not intended to differentiate these two factors.

There is considerable evidence indicating that airway cooling or airway water loss can cause respiratory disturbances. It was shown that after the inhalation of cold air the airway resistance increased markedly in patients with respiratory disease.

Wells, R. E. Jr., J. E. C. Walker, and R. B. Hickler. 1960. Effects of cold air on respiratory airflow resistance in patients with respiratory-tract disease. *N. Engl. J. Med.* 263:268-273.

In animal studies, it was reported that the airway clearance rate decreases as the intratracheal temperature falls.

Baetjer, A. M. 1967. Effect of ambient temperature and vapor pressure on ciliamucus clearance rate. *J. Appl. Physiol.* 23:498-504.

Impairment of mucociliary transport was observed in dogs after breathing dry air.

Hirsch, J. A., J. L. Tokayer, M. J. Robinson, and M. A. Sackner. 1975. Effects of dry air and subsequent humidification on tracheal mucous velocity in dogs. *J. Appl. Physiol.* 39:242-246.

Although the healthy respiratory tract may be able to withstand certain heat and water losses, the airways of patients with respiratory disease appear to be liable to this negative heat and water balance. This is especially apparent when the rate of loss is accelerated, as in exercise.

Figure 6:
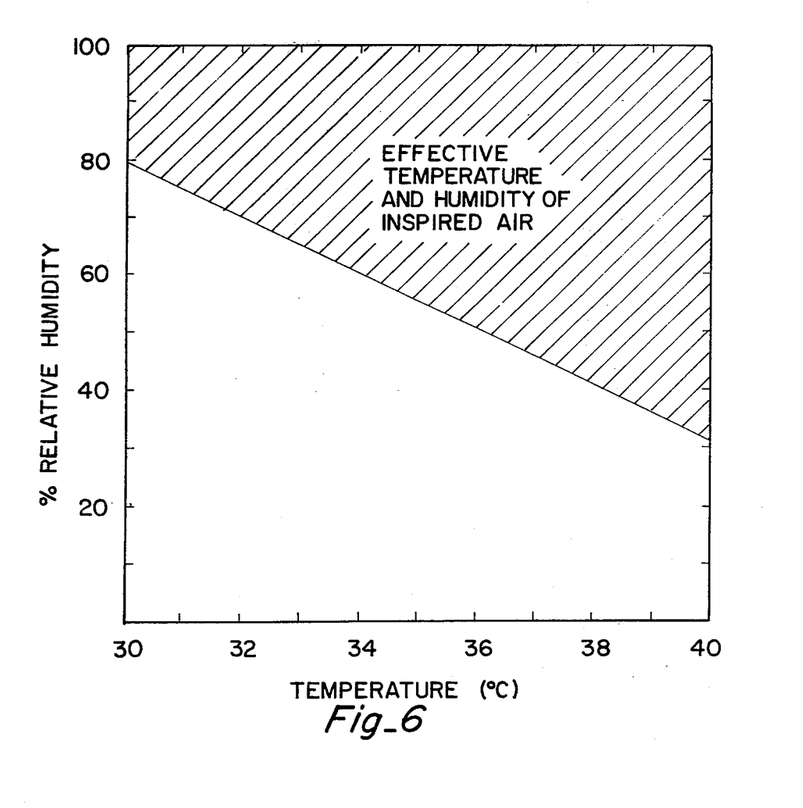
FIG. 6 is a graph showing the effective temperature and humidity of inspired air to substantially minimize heat and water loss from the respiratory tract for alleviating asthma attacks.

Based upon the above discussed results, the effective temperature and humidity range for substantially reducing heat and water loss in the respiratory tract to alleviate asthmatic attacks is apparently that shown in FIG. 6. For example, at 30° C., the range of effective humidity would be between 80% and 100% RH. While at 40° C., the effective range of humidity would be substantially between 30% and 100% RH. Exercise-induced asthma attacks are inhibited by inspiring air between 37° C. to 40° C. and 80% RH to 100% RH. Exercise-induced asthma attacks were clearly prevented by inspiring air between 37° C. to 40° C. at 100% RH.

Figures 7, 8, 10:
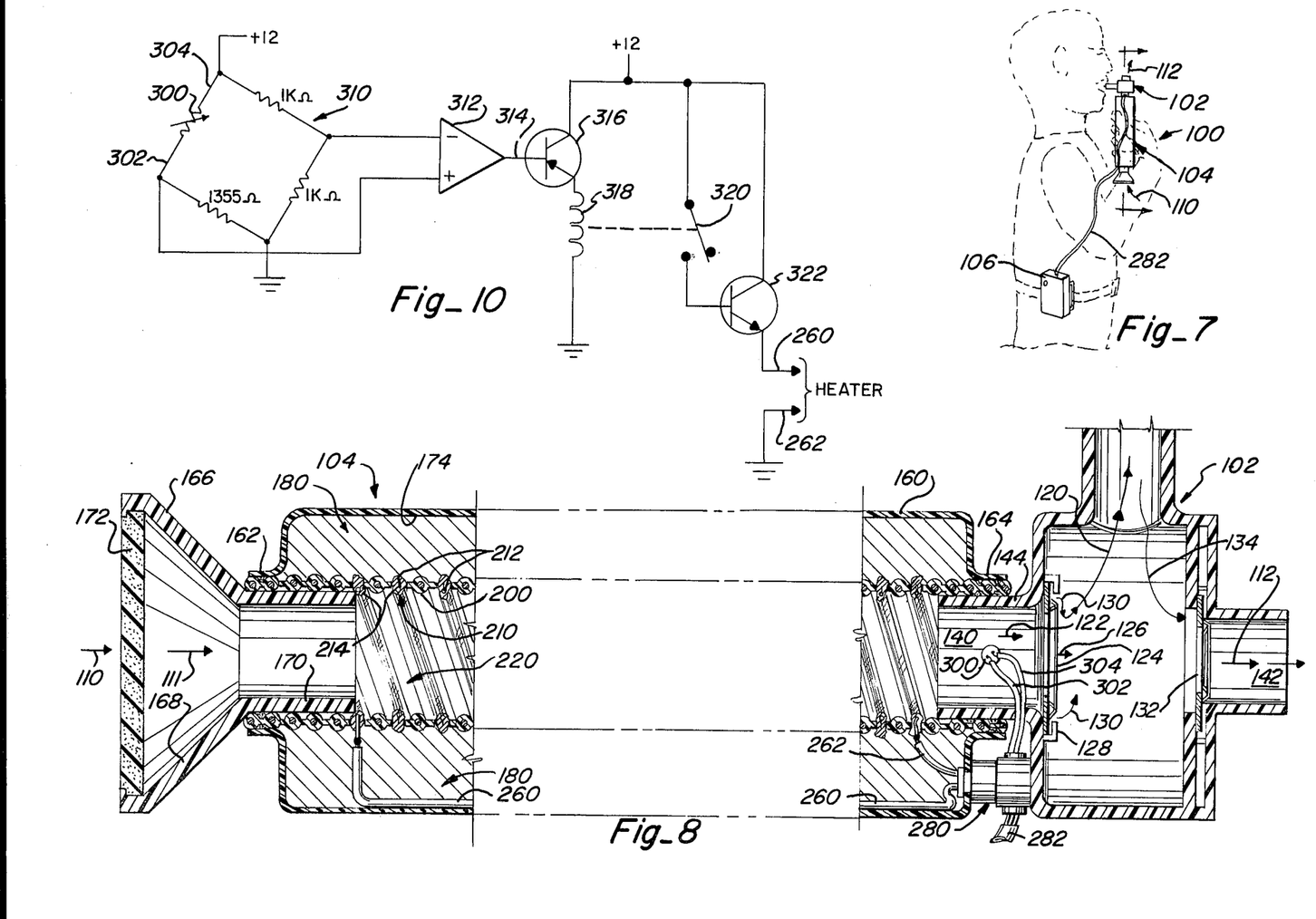
FIG. 7 is a graphical illustration of a portable apparatus of the second embodiment for alleviating asthma attacks of an asthma sufferer.
FIG. 8 is a cross-section of the portable apparatus of FIG. 7 illustrating the various components thereof.
FIG. 10 is an electronic schematic of the control circuit for the portable apparatus of FIG. 7.
Figure 9:
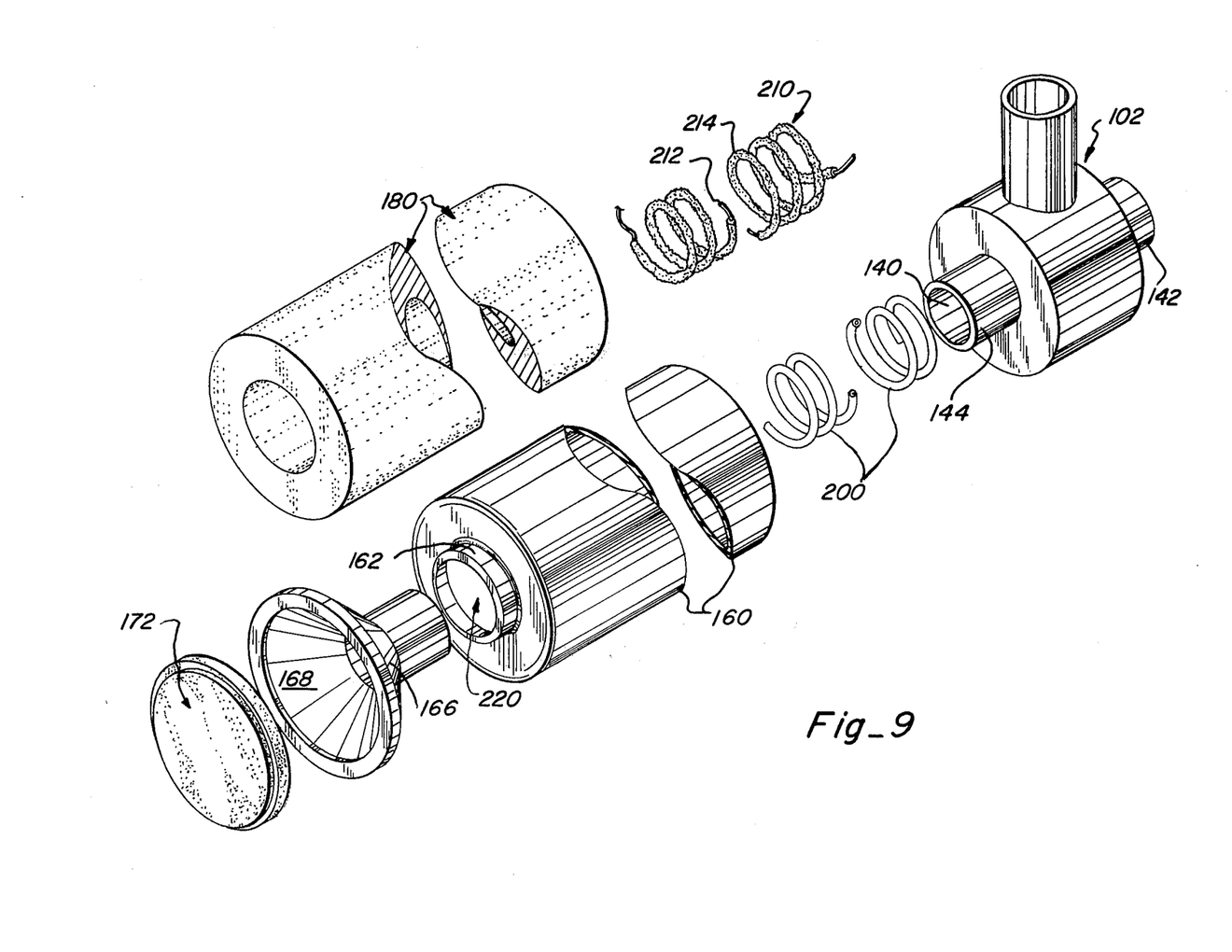
FIG. 9 is an exploded perspective representation of the various components of the portable apparatus of FIG. 7.

A second preferred embodiment of the present invention is shown as the portable apparatus 100 in FIG. 7. Apparatus 100 includes a mouthpiece 102, a heat and water vapor generator 104 and a portable battery 106. The asthmatic sufferer inhales through mouthpiece 102 warm and humidified air modified within the interior of the generator 104.

In operation, atmospheric air 110 is received by the generator 104 and is stored therein until the asthma sufferer exhales air 112. At this time, the asthma sufferer will inhale the stored heated and humidified air from the interior of the generator 104 while at the same time causing the generator 104 to intake additional atmospheric air 110. The generator 104 is designed to heat and humidify the air to a desired temperature and humidity level. A portion of the generator 104, as will be subsequently discussed, may be made disposable so that after each use, the disposable portion is thrown away and a new portion is inserted just prior to the next use.

The mouth valve 102 is conventional and may comprise any of a number of commercially available mouth valves or tent masks. In the mouth valve 102 of FIG. 8, the air flow upon inspiration is shown by arrows 122, 130, and 120. A flap 124 is biased upwardly in the direction of arrow 126 to allow the air 122 to flow outwardly from the sides of a holder 128 as shown by arrows 130. At the same time a second flap 132 is biased in the closed position. When exhaling, air flows in the direction of arrow 134, and outwardly into the flow of 112. As mentioned, the valve 102 can comprise any of a number of commercially available valves which function to input air from one passageway into the mouth and to output air through a second separated passageway. Passageways 140 and 142 in the preferred embodiment of FIG. 8 diametrically oppose each other and extend outwardly in a cylindrical fashion from the valve 102. The outward protuberance 144 containing passageway 140 engages generator 104.

The generator 104 comprises an outer tubular surface 160 having oppositely directed, opposing ends 162 and 164 of substantially lesser diameter than tubular surface 160. End 164 has a diameter substantially the same as the outer diameter of extension 144 of valve 102. In this manner, the tubular portion 160 can be firmly affixed to extension 144 by expanding end 164 over the outer cylindrical surface of the extension 144. The end 162 of the tubular portion 160 in a similar manner fits over the outer surface of a funnel 166.

Funnel 166 can be a preformed injected molded plastic part substantially in the configuration as shown in FIG. 8 wherein a hopper portion 168 and an extension portion 170 is formed. Disposed in the end of the funnel portion 168 is a filter 172 for filtering out any particulate matter found within the atmospheric air 110. The funnel 166 serves to direct atmospheric air 110 through the filter 172 and into the interior air of the tubular portion 160.

Disposed against the inner surface 174 of the tubular portion 160 is a material 180 designed to store or hold water. The water absorbent material 180 extends from the inner surface 174 of the tubular portion 160 to a core area substantially equal to the inner diameter of ends 162 and 164. Disposed around the central core portion and firmly abutting the absorbent material 180 is a coiled support 200. The support 200 lends structure to the generator 104, and firmly holds the absorbent material 180 against the inner surface 174 of the tubular member 160.

As indicated in FIG. 8, disposed between each coil of the support 200 is intertwined a heating coil 210. Heating coil 210 is comprised of a central coil heating filament 212 and an outer covering material 214.

In the preferred embodiment, the saturated material 180 can comprise any material that has a capacity for storage of water including fibrous, plastic, or sponge-like material. The covering material 214 around the filament can also be any water-carrying material such as fiber or sponge. In operation, the water found within material 180 is delivered by capillary action into the covering material 214 and near the filament 212 so that the water is heated and evaporated into the central core area 220 of the generator 104. The central core area 220, of course, is hollow from end 162 to end 164.

The ends of the filament are interconnected over leads 260 and 262 through a connector 280 and into a cable 282. A thermistor 300 is disposed in formed passageway 140 and is interconnected over lead 302 and 304 with connector 280 and also into the cable 282.

FIG. 10 illustrates the electronic diagram of the thermistor control circuit located near the battery. The input from thermistor 300 is delivered over lead 302 and 304 into a Wheatstone bridge 310 which is sensitive to current or voltage imbalance. The Wheatstone bridge 310 is designed as shown in FIG. 10 with those particular values to turn on at 36.7° C. and to turn off at 36.9° C. Operational amplifier 312 senses the voltage imbalance of the Wheatstone bridge 310 and delivers that as a step output on lead 314 to either turn on or turn off transistor 316. The emitter of transistor 316 is connected through coil 318 to ground and the collector of transistor 316 is connected to positive voltage. When current flows through coil 318, relay switch 320 is closed to provide positive voltage to the base of transistor 322. The collector of transistor 322 is connected to positive voltage and the emitter is connected through to lead 260 which accesses one end of the coiled heater 212, the other end of which is delivered over lead 262 to ground.

The operation of the portable apparatus of the present invention will now be discussed. When an asthma sufferer inhales air 120, air existing in the core area 220 of the generator 104 is delivered into the lungs of the sufferer. That air is replaced by new atmospheric air 110 passing through a filter 172 and into a funnel 166 that directs the filtered air 111 into the core area 220. By the time the sufferer inhales again, that new atmospheric and filtered air 111 is humidified and heated to a predetermined desired temperature which for the circuitry shown in FIG. 10 is 37° C. by means of the heating filament 212. If the incoming fresh air has a lower temperature than desired, the thermistor 300 detects a temperature below 36.7° C., a voltage is produced on lead 314 to turn transistor 316 on which activates the relay coil 318 to close switch 320 thereby turning on switch 322 to activate the heater. During this time, the heating filament 212 is on to bring the newly stored air 111 up to a temperature of 37° C. The operational amplifier 312, however, turns off at 36.9° C., since sufficient thermal lag exists in the heater coil 212 to bring the temperature of the stored air up to 37° C. During this process, water is being evaporated into the stored air through the covering material 214 and thence to the surface of the filament thereby causing evaporation. The storage material 180 is designed to store enough water to last the typical asthma sufferer more than one hour of use. The water is drawn from the material 180 through the fibers 214 to the surface of the filament 212 by means of capillary action. Therefore, with the next inhalation, the air in the core area 220 is inputted into the lungs of the sufferer having the desired temperature and the desired humidity. The percentage saturation of humidity in the air can be varied by varying the physical length of the tube 160 and the corresponding lengths of material 180 and filament 212. The longer the tube 160 is, the more humid the air will become within the time interval between two successive inhalations.

Of course, expired air 134 is delivered out from the mouthpiece 102 through passageway 142 to the atmosphere at a point remote from the intake of atmospheric air 110 at the funnel 166.

The generator 104 is designed to be disposable and can be pulled off of extension 144 of the mouth valve 102 and thrown away. Therefore, after each use, a new generator 104 is inserted over extension 144 and used by the asthma sufferer. The connector 280 is fixedly attached to the mouthpiece 102 and when the generator 104 is firmly in position, the filament leads are interconnected with cable 282.

In actual use, the sufferer would wear the portable apparatus as long as he is in a hyperventilated state. Therefore, before exercising, the sufferer would place the portable apparatus into his mouth or, if using, a tent mask or other conventional input he may affix the portable apparatus to his head in a conventional manner such as tying it around the head region. The sufferer can now exercise and hyperventilate. After exercising, the sufferer may still be hyperventilating and he should continue to wear the apparatus until he has rested and his breathing is normal.

While the portable preferred embodiment uses a storage area to heat and humidify the air during the time span of expiration and inspiration, such an arrangement is presented as a means for conserving power consumption in the battery. If conservation of energy was not a concern, then the warm, humidified air can be pumped continuously to the sufferer for breathing. Indeed, while the present embodiment illustrates a mouth intake and a tube, the teachings of the present invention may be utilized to adapt the apparatus into a helmet, backpack, or other suitable portable arrangement.

Under the teachings of this invention, any suitable fluid may be vaporized into a gas to increase the heat content of the inspired air in order to reduce the heat loss in the respiratory tract (also termed the airways or respiratory system) of an asthma sufferer. Since air has a low specific heat, the added gas must have a higher specific heat in order to provide sufficient heat content to reduce the heat loss within the respiratory tract.

Although the present invention has been described with a certain degree of particularity, it is understood that the present disclosure has been made by way of example and that changes in details of structure may be made without departing from the spirit thereof.

I claim:

1. Respirator apparatus adapted for use by an asthma sufferer in alleviating asthma attacks, said apparatus comprising:

an elongated tubular body defining a central passage extending axially through the body including air intake means at one end of said central passage and means for storing air within said central passage, means including a water absorbent layer disposed in outer concentric relation to said central passage cooperative with said storing means for passing vaporized water from said absorbent layer, through said tubular body and into the air stored within said central passage, heating means interposed between said water absorbent layer and said central passage for heating and vaporizing water adapted to be stored in said absorbent layer to a predetermined temperature and humidity level for intermixture with the air stored in the central passage, and delivery means at the end of said central passage opposite to said intake means being operative in response to inhalation by the asthma sufferer for delivering the intermixture of vaporized water and air into the respiratory tract.

2. Respirator apparatus in accordance with claim 1 wherein said intake means is defined by a generally funnel-shaped inlet having a filter disposed thereacross to filter the air as it is drawn into said central passage.

3. Respirator apparatus in accordance with claim 2 wherein said heating means vaporizes the water to raise the humidity of the air in the central passage in the range of 30% to 100% relative humidity said elongated tubular body including an outer shell and an inner coiled support spaced concentrically within said shell with said water absorbent layer sandwiched therebetween.

4. Respirator apparatus in accordance with claim 3 in which said heating means includes a portable electric power source having a battery adapted to be located on said asthma sufferer, a heating filament cylindrically coiled along the inner surface of said water absorbent layer, said heating filament being connected to said battery, and said heating means operative to maintain the temperature level in the range of 30° C. to 40° C.

5. Respirator apparatus in accordance with claim 4 including water conducting means disposed around said filament for conducting water from said water absorbent layer to the surface of said heating filament.

6. Respirator apparatus in accordance with claim 4 including temperature control means responsive to the temperature of air in said central passage for controlling the electrical current from said battery to said heating filament whereby to maintain a predetermined temperature level.

7. Respirator apparatus in accordance with claim 1 said delivery means including valve means responsive to inhalation by the asthma sufferer for inducing the flow of vaporized air from the central passage into the respiratory tract, and said intake means defined by a convergent air intake member having a filter member disposed thereacross.

8. Portable respirator apparatus adapted to be located on the body of a person for modifying air prior to inhalation, said apparatus comprising:

an enongated, disposable tubular body having an outer cylindrical shell and an inner spaced concentric coiled support in surrounding relation to a central air passage extending axially through said body, air intake means at one end of said central passage and valve means at the opposite ends of said central passage operative to act as a temporary closure across the opposite end of said passage whereby to store air induced to flow through said air intake means within said central passage, water retention means in the form of a water absorbent layer interposed between said outer shell and said coiled support containing water in said water absorbent layer, heating means disposed along the inner surface of said water absorbent layer in outer concentric relation to said central air passage being operative to vaporize water from said water absorbent layer through said coiled support while permitting it to mix with the air stored in said central passage, and said valve means being operative in response to inhalation by the asthma sufferer to permit the air stored in said central passage to pass into the respiratory system of the asthma sufferer while inducing the flow of additional air through said air intake means into said central passage.

9. Respirator apparatus according to claim 8 further characterized by said heating means being in the form of a coiled heat filament substantially coextensive with said coiled support.

10. Respirator apparatus according to claim 9 in which said heating means further includes a portable electrical power source adapted to be located on said asthma sufferer, and temperature control means associated with said heating filament for controlling the temperature of the vaporized air stored in said central passage.

11. Respirator apparatus according to claim 8, said air intake means, central air passage and valve means being located in coaxial relationship to one another.

12. Respirator apparatus according to claim 11, said air intake means being funnel-shaped to converge inwardly for connection to said central air passage, and a filter disposed at the outer divergent end of said funnel-shaped air intake means.

13. Respirator apparatus according to claim 8, said water absorbent layer comprising inner and outer concentric water absorbent layer portions, said inner concentric layer portion covering said heating filament and the water in said inner concentric layer portion being heated by said heating filament and evaporated into said central air passage.

* * * * *